(12) United States Patent
Kobayashi et al.

(10) Patent No.: US 6,273,566 B1
(45) Date of Patent: Aug. 14, 2001

(54) OPHTHALMOLOGIC CHARACTERISTIC MEASURING APPARATUS

(75) Inventors: Katsuhiko Kobayashi; Toshifumi Mihashi, both of Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 09/672,543

(22) Filed: Sep. 28, 2000

(30) Foreign Application Priority Data

Sep. 28, 1999 (JP) .................................................. 11-275375

(51) Int. Cl.$^7$ ...................................................... A61B 3/10
(52) U.S. Cl. ............................................................. 351/221
(58) Field of Search ............................... 351/205, 206, 351/211, 212, 221, 237, 243, 246

(56) References Cited

U.S. PATENT DOCUMENTS 4,444,476 * 4/1984 Simon et al. ........................ 351/211
5,129,720 * 7/1992 Jovicevic ............................. 351/243

* cited by examiner

Primary Examiner—George Manuel
(74) Attorney, Agent, or Firm—Baker Botts L.L.P.

(57) ABSTRACT

An object of the present invention is to provide an ophthalmologic characteristic measuring apparatus for precisely measuring optical characteristics of the eye to be examined and allowing the examiner to readily understand how an optotype is seen by the eye. The ophthalmologic characteristic measuring apparatus according to the present invention comprises an illuminating optical system for illuminating a microscopic area on the retina of the eye to be examined with light rays emitted from a light source unit; a light receiving optical system for guiding the light rays reflected from the retina of the eye to a light receiving unit; an arithmetic unit for determining optical characteristics of the eye including refractive powers and other components of the eye based on a signal from the light receiving unit, and calculating index image data representing the way in which a specified optotype is observed by the eye when a specified refractive power is corrected; and a display unit for displaying an index image representing the way in which the optotype is observed by the eye, based on the index image data.

5 Claims, 13 Drawing Sheets

FIG. 5
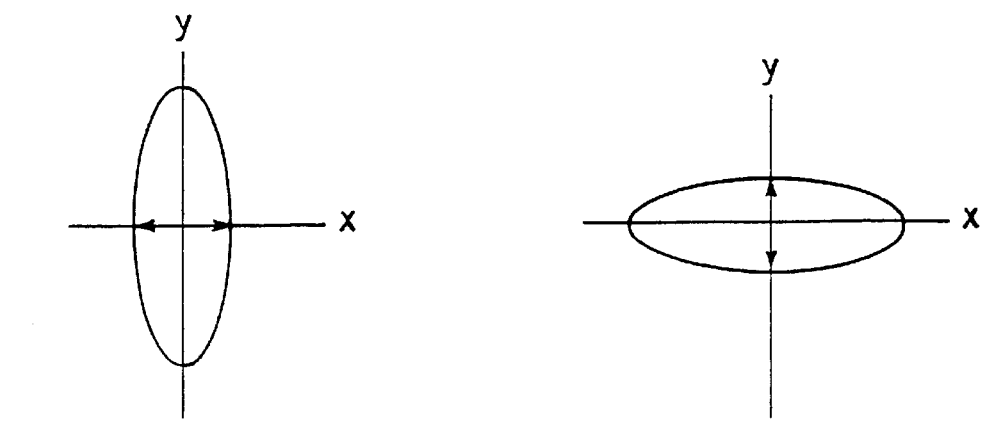
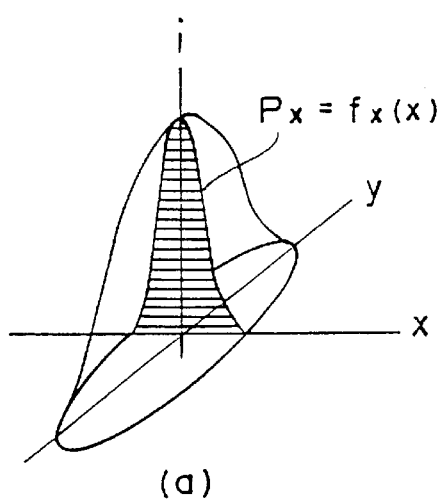
(a)
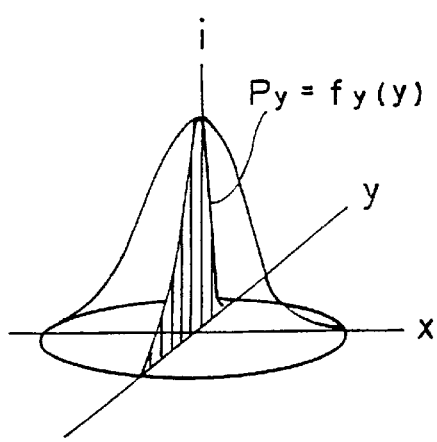
(b)
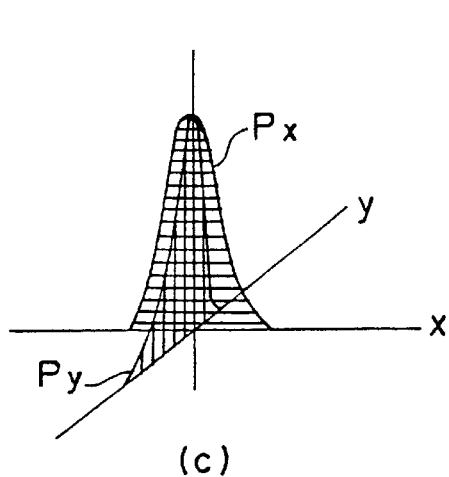
(c)
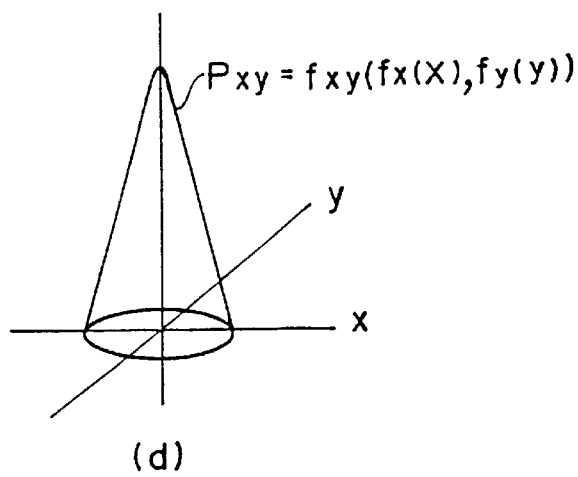
(d)

$I xy = O xy * P xy$

FIG. 7.
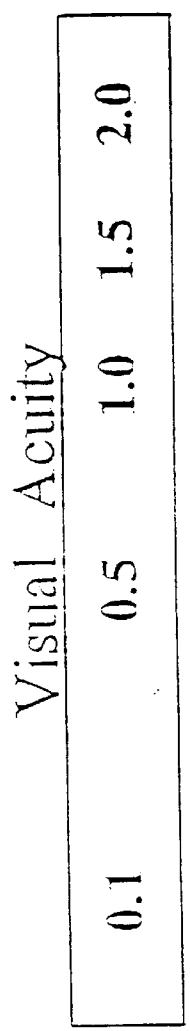
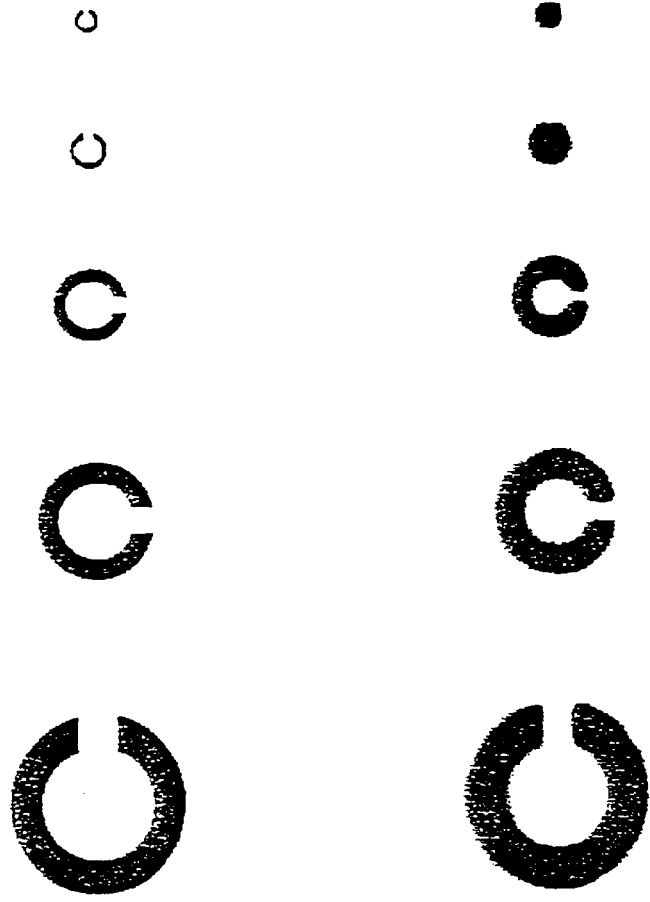

OPHTHALMOLOGIC CHARACTERISTIC MEASURING APPARATUS

BACKGROUND OF THE INVENTION

The present invention relates to an ophthalmologic characteristic measuring apparatus for precisely measuring optical characteristics of the eye to be examined and allowing the examiner to readily understand how an optotype is seen by the eye.

There is conventionally proposed an apparatus configured in such a manner that a subjective optometry device is used for the subject to look at an optotype via a correction lens provided according to the eyesight of the subject, and a point image intensity distribution corresponding to optical characteristics of the eye is measured by using the correction lens system, so that an index image that is actually observed by the eye is calculated from the measured point image intensity distribution and the index image is displayed.

With this apparatus, the examiner observes the index image obtained by arithmetic, and changes one correction lens for another to bring the index image into an optimally focused state, so that the refractive power of the eye can be determined from the amount of correction when the optimum correction lens selected by the examiner is used. Thus, the apparatus has an advantage of eliminating errors in response from the subject, thereby making it possible to perform accurate eye examination.

With this conventional apparatus, however, the examiner needs to perform correction by using correction lenses while observing an index image displayed by arithmetic. This not only results in difficulty in the operation for eye examination, which is a burden on the examiner, but also will cause a pain and a burden to the subject because it takes time for the eye to be examined.

An object of the present invention is to solve this problem of the conventional technique. Another object of the present invention is to provide an ophthalmologic characteristic measuring apparatus that makes it possible to readily observe in a single measurement an image seen by the subject when the subject wears an appropriate correction lens, and therefore perform accurate eye examination in a short time.

SUMMARY OF THE INVENTION

According to the present invention, there is provided an ophthalmologic characteristic measuring apparatus for precisely measuring optical characteristics of the eye to be examined and allowing the examiner to readily understand how an optotype is seen by the eye. The ophthalmologic characteristic measuring apparatus comprises an illuminating optical system for illuminating a microscopic area on the retina of the eye to be examined with light rays emitted from a light source unit; a light receiving optical system for guiding the light rays reflected from the retina of the eye to a light receiving unit; an arithmetic unit for determining optical characteristics of the eye including refractive powers and other components of the eye based on a signal from the light receiving unit, and calculating index image data representing the way in which a specified optotype is observed by the eye when a specified refractive power is corrected; and a display unit for displaying an index image representing the way in which the optotype is observed by the eye, based on the index image data.

BRIEF DESCRIPTION OF THE DRAWINGS

Preferred embodiments of the present invention are illustrated in the accompanying drawings in which:

FIGS. 5(*a*) to 5(*d*) are a diagram of assistance in explaining two-dimensional PSF (point image intensity distribution);

FIG. 6 is a diagram of assistance in explaining an optotype $O_{xy}$ and an image $I_{xy}$;

FIG. 7 is a diagram of assistance in explaining an image $I_{xy}$ displayed on a display means 84;

DESCRIPTION OF THE INVENTION

Preferred embodiments of the present invention will be described with reference to the accompanying drawings.

[First embodiment]

Figure 1:
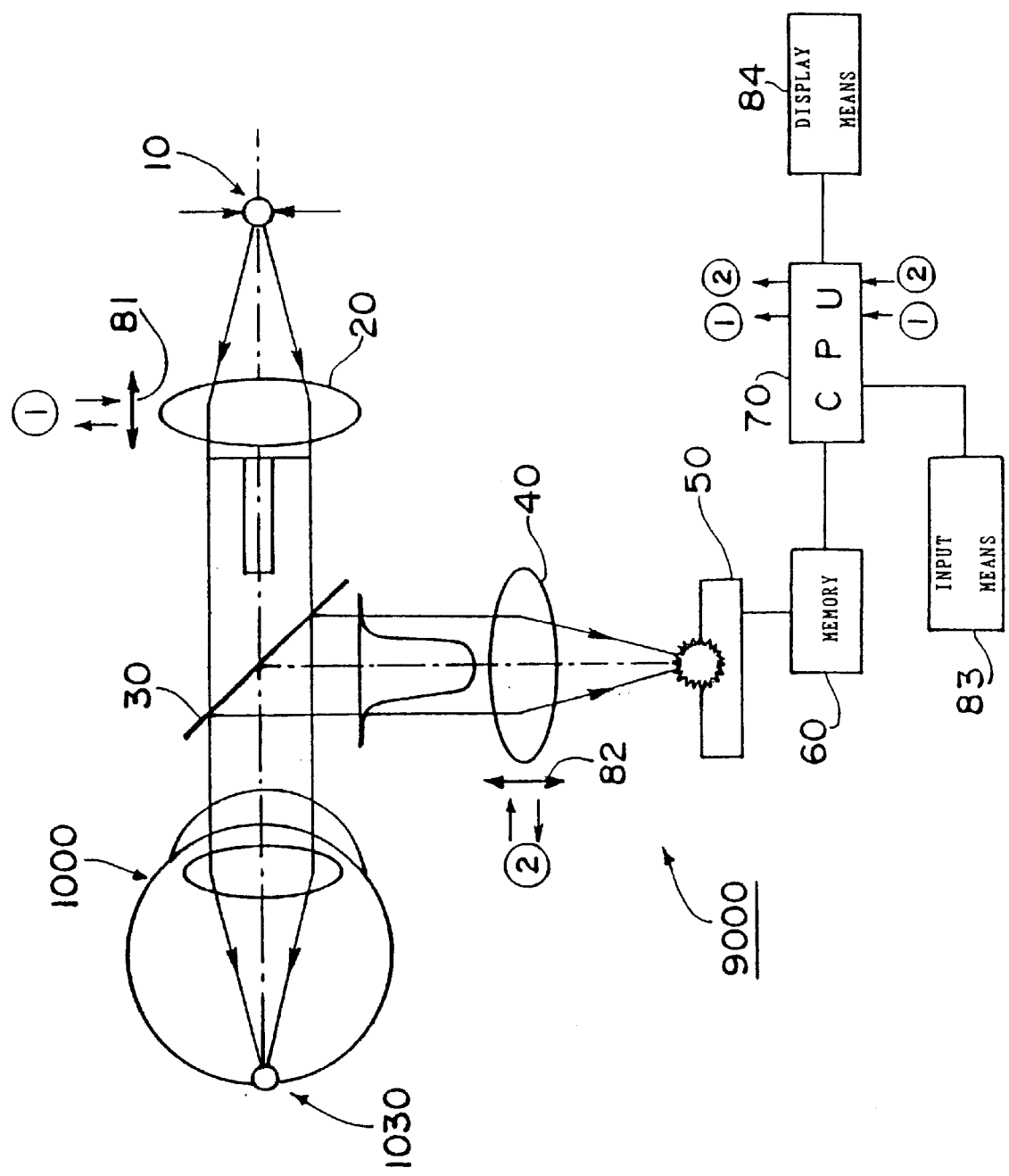
FIG. 1 shows the configuration of an optical measuring apparatus 9000 of a first embodiment of the present invention.

As shown in FIG. 1, an optical characteristic measuring apparatus 9000 of the first embodiment comprises a light source unit 10, a projecting lens 20, a beam splitter 30, a focusing lens 40, an imaging device 50, a memory means 60, a CPU 70, a projecting lens moving means 81, a focusing lens driving means 82, an input means 83, and a display means 84.

The light source unit 10 is a point light source placed at the focal point of the projecting lens 20. The projecting lens 20 collimates light rays from the light source unit 10 and causes the parallel light rays to fall on an eye 1000 to be examined, so that an image is formed on the retina 1030 of the eye to be examined.

The beam splitter 30 reflects the light reflected from the retina 1030 of the eye to be examined and deflects the light in the direction of the focusing lens 40. Incidentally, the beam splitter 30 is designed to transmit the light from the projecting lens 20.

The focusing lens 40 focuses the light reflected from the retina 1030 of the eye to be examined on the imaging device 50. The imaging device 50 corresponds to a light receiving unit comprising an imaging device such as a CCD, and converts an image taken into an image signal. The memory means 60 corresponds to a memory unit, and is a frame memory for storing image signals from the imaging device 50.

The projecting lens moving means 81 is a focusing mechanism for moving the projecting lens 20 to achieve focus. The projecting lens moving means 81 corresponds to a focus adjusting means. Similarly, the focusing lens driving means 82 is a focusing mechanism for moving the focusing lens 40 to achieve focus. The focusing lens driving means 82 corresponds to a focus adjusting means. Incidentally, the projecting lens moving means 81 and the focusing lens driving means 82 are provided with a means for detecting the amount of movement, such as an encoder, so that the amounts of movement of the lenses can be detected.

The CPU 70 controls the entire optical characteristic measuring apparatus 9000 of the first embodiment. Also, the CPU 70 sequentially detects the amounts by which the projecting lens 20 and the focusing lens 40 are moved by the projecting lens moving means 81 and the focusing lens driving means 82 respectively, and stores in the memory means 60 image signals from the imaging device 50 that correspond to positions when the lenses are moved. Then the CPU 70 performs various operations based on the positions to which the projecting lens 20 and the focusing lens 40 are moved by the projecting lens moving means 81 and the focusing lens driving means 82 respectively, as well as the image signals stored in the memory means 60 that correspond to the positions. Incidentally, the configuration including the CPU 70 corresponds to an arithmetic unit.

The input means 83 is provided for the examiner to input data and processing instructions. The display means 84 corresponds to a display unit, and displays an image on the retina of the eye after correction by a eyeglass lens 90000, which image is calculated and estimated by the optical characteristic measuring apparatus 9000.

Incidentally, the light source unit 10 and the projecting lens 20 correspond to an illuminating optical system, while the beam splitter 30 and the focusing lens 40 correspond to a light receiving optical system.

Figure 2:
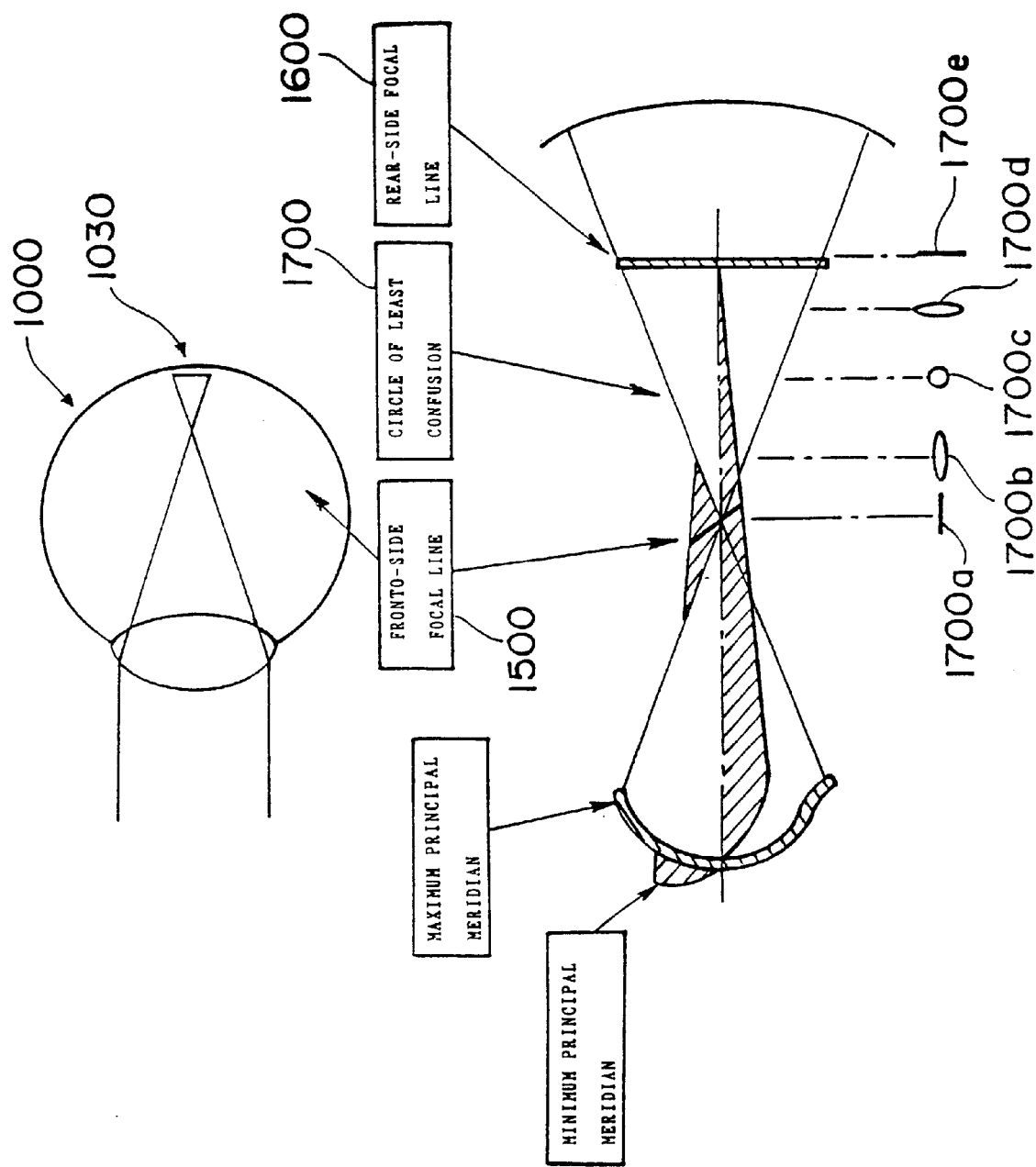
FIG. 2 schematically shows the state of light rays in a compound myopic astigmatism eye 1000.

The procedure for estimating corrected eyesight by using this optical arrangement will be described with respect to a compound myopic astigmatism eye 1000 to be examined, which is shown in FIG. 2. In the case of compound myopic astigmatism, the curvature of the front of the cornea 1010 in the vertical direction and the curvature of the front of the cornea 1010 in the horizontal direction with respect to incident parallel light rays are different from each other, as shown in FIG. 2. Therefore, optical astigmatism or so-called distorted vision is caused.

Because of the astigmatism, the focal point is not present. Instead, there are a front-side focal line 1500, a rear-side focal line 1600, and circles of least confusion (also called focal circles) 1700$a$, 1700$b$, 1700$c$ . . . at positions where the light rays becomes smallest in the middle of the front-side focal line 1500 and the rear-side focal line 1600.

Compound myopic astigmatism is characterized in that the curvature of the front of the cornea 1010 in the vertical direction is stronger than the curvature of the front of the cornea 1010 in the horizontal direction, and the front-side focal line 1500 and the rear-side focal line 1600 are both present on the front side of the retina 1030.

Figure 3:
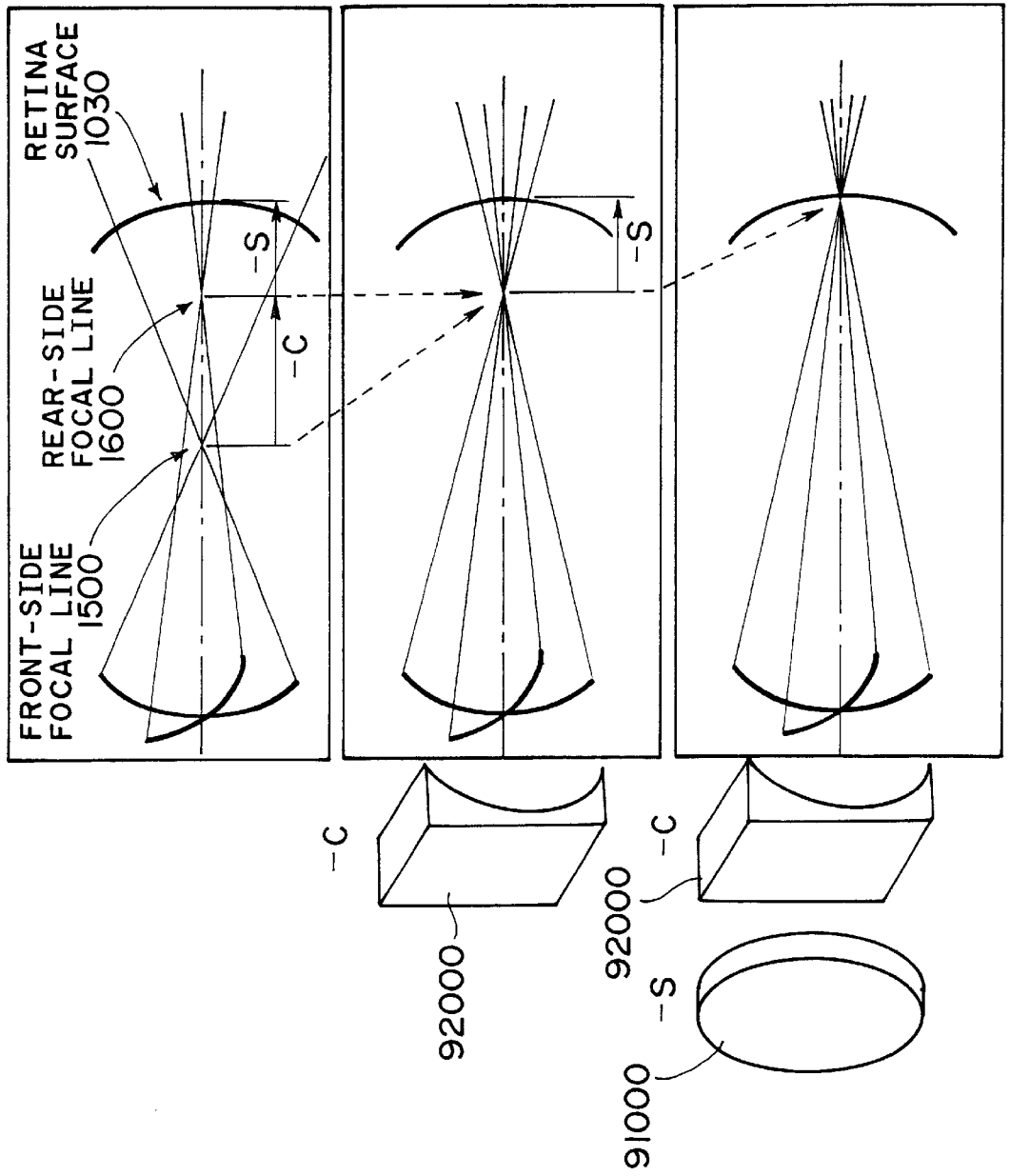
FIG. 3 is a diagram of assistance in explaining the principle of astigmatism correction with an eyeglass 90000.

When the eye 1000 to be examined is corrected by an eyeglass lens 90000, the correction is performed, as shown in FIG. 3, by using a spherical lens 91000 with a refractive power of -S diopters and a concave lens 92000 with a refractive power of -C diopters and with its axes aligned with the maximum principal meridian and the minimum principal meridian.

Eyeground images of the front-side focal line 1500, the rear-side focal line 1600, and the circles of least confusion 1700$a$, 1700$b$, 1700$c$ . . . can be obtained by moving the projecting lens 20 and the focusing lens 40 shown in FIG. 1. The eyeground images are captured by the imaging device 50 as images. Also, data corresponding to the refractive powers of the spherical lens 91000, which has a refractive power of -S diopters, and the concave lens 92000, which has a refractive power of -C diopters, can be obtained from the amounts of movement of the projecting lens 20 and the focusing lens 40.

More specifically, FIG. 2 schematically shows the compound myopic astigmatism eye 1000 to be examined and shows the state of the light rays when the projecting lens 20 or the focusing lens 40 is located at a reference position $X_0$. As the projecting lens 20 and the focusing lens 40 are moved, an image of a circle of least confusion 1700 is formed on the eyeground. An image that corresponds to the image of the circle of least confusion 1700 is formed in the imaging device 50, and its image signal is recorded in the memory means 60 together with the amount of movement of the projecting lens 20 as described above. The front-side focal line 1500 and the rear-side focal line 1600 are determined from the image signal recorded in the memory means 60. Suppose that the position of the projecting lens 20 that corresponds to one of the image signals is $X_1$, and that the position of the focusing lens 40 that corresponds to the image signal is $X_2$. Then, $|X_1-X_2|$ corresponds to astigmatic power, and $|X_1|$ corresponds to spherical power.

It should be noted that the S diopters of the spherical lens 91000 corresponds to spherical power in terms of optical aberration. If the eye 1000 to be examined has an optical aberration only with a spherical power (-S) and astigmatism (-C), the incident parallel light rays can be focused on the retina 1030 by performing the above-mentioned correction, as shown in FIG. 3. As a result, the subject examined will acquire considerably good eyesight by the above-mentioned correction if the subject examined has no disorders in the retina 1030 and other parts after the retina 1030.

Figure 4:
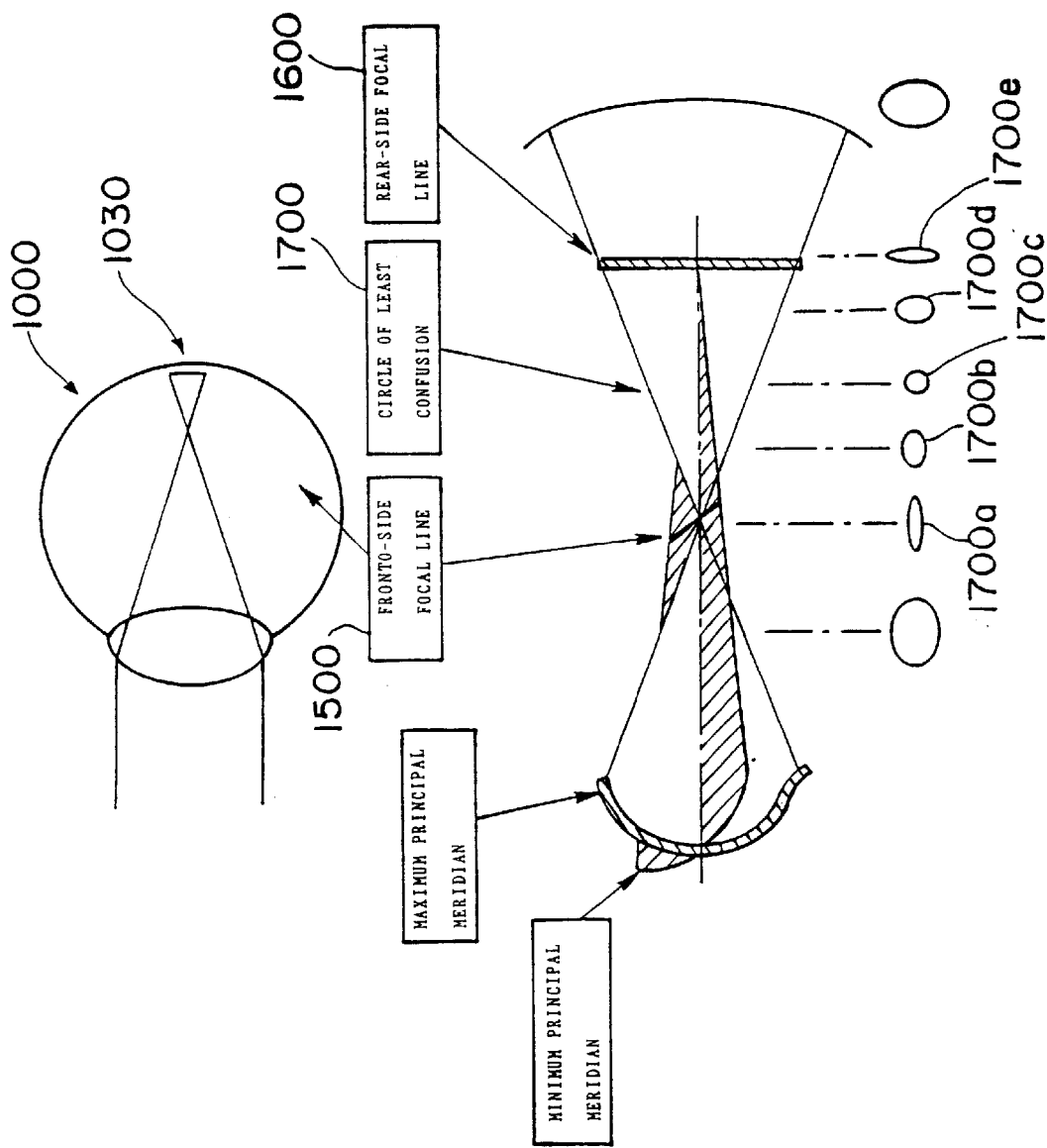
FIG. 4 schematically shows the state of light rays in an eye 1000 that has astigmatism and other factors.

In addition, as shown in FIG. 4, the eye 1000 to be examined may have factors that lower the optical performance of the eye other than spherical power (-S) and astigmatism (-C), such as spherical aberration, coma aberration, and other irregular optical aberrations, or scattering and opacity due to a cataract and the like. In this case, a front-side focal line 1500 and a rear-side focal line 1600 obtained by the above-mentioned measurement will become less clear than the front-side focal line 1500 and the rear-side focal line 1600 mentioned above.

FIGS. 5($a$) to 5($d$) show a so-called Point Spread Function which represents a front-side focal line 1500 and a rear-side focal line 1600 as light intensity distributions.

The light intensity distribution of a rear-side focal line 1600 is shown in FIG. 5($a$).

$P_x=f_x(x)$ representing a section in the X direction shows the light intensity distribution in the direction in which the light rays of the rear-side focal line 1600 are most focused.

Similarly, the light intensity distribution of the front-side focal line 1500 or $P_y=f_y(y)$ representing a section in the Y direction shows the light intensity distribution in the direction in which the light rays of the front-side focal line 1500 are most focused. These light intensity distributions are calculated by an arithmetic processing means including the CPU 70 from an image signal from the imaging device 50.

Two-dimensional PSF (point image intensity distribution) is expressed by elliptic approximation at light intensity I (i), as shown in FIGS. 5($c$) and ($d$).

For example, in FIG. 5($d$), two-dimensional PSF (point image intensity distribution) is calculated as $P_{xy}=f_{xy}(f_x(x), f_y(y))$. PXy shows PSF on the retina 1030 of the eye 1000 that is obtained when the eye 1000 is corrected with an eyeglass lens 90000 which combines a spherical lens 91000 with a refractive power of -S diopters and a cylindrical lens 92000 with a refractive power of -C diopters.

As shown in FIG. 6, $P_{xy}$ obtained in the manner described above is combined with the optotype $O_{xy}$ that the eye being examined 1000 is actually looking at, and is then integrated to obtain an image $I_{xy}$. The image $I_{xy}$ shows an image on the retina 1030 of the eye 1000 that is obtained when the eye 1000 is corrected with the eyeglass lens 90000 which combines the spherical lens 91000 with a refractive power of -S diopters and the cylindrical lens 92000 with a refractive power of -C diopters. This means that the image $I_{xy}$ can be displayed on the display means 84, as shown in FIG. 7.

It should be noted that ophthalmologic characteristics correspond to refractive powers (spherical power, astigmatic power, and astigmatic axis) and other factors such as irregular astigmatism components, scattering, and opacity.

The procedure described above makes it possible to estimate an image on the retina 1030 of the subject examined that will be actually obtained after correction with the eyeglass lens 90000, by measuring the eye 1000 to be examined with the optical characteristic measuring apparatus 9000 of the first embodiment of the present invention.

Specifically, the first embodiment of the present invention makes it possible to automatically and objectively measure accurate optical characteristics of the eye including the refractive powers (spherical power, astigmatic power, and astigmatic axis) and the irregular astigmatism components of the eye, which can be corrected with an eyeglass lens 90000. Also the first embodiment of the present invention makes it possible to, based on the result of the above measurement, display on the display means 84 an index image observed by the subject when the subject wears an appropriate eyeglass lens 90000. Thus, the examiner can easily understand in a single measurement the extent to which the eye to be examined can be corrected with an eyeglass lens 90000. In addition, according to the first embodiment of the present invention, changes in the image of the index when the refractive power of the correction lens is changed can be displayed by arithmetic without performing another measurement. Therefore, the examiner can readily perform simulation to decide the refractive power of the eyeglass lens to be prescribed to the subject examined.

In the first embodiment, description has been made with respect to compound myopic astigmatism. However, eyes with other refraction irregularities can also be measured.

In the first embodiment, an image on the retina of the eye is estimated by PSF that is obtained after correction based on information on a front-side focal line 1500 and a rear-side focal line 1600. However, it is also possible to estimate an image on the retina of the eye when an arbitrary eyeglass lens 90000 is used, by using PSF that is corrected based on information obtained from the refractive power of the arbitrary eyeglass lens 90000.

It is also possible to calculate MTF from PSF that is obtained based on information on a front-side focal line 1500 and a rear-side focal line 1600, and estimate an image on the retina of the eye when the characteristics of MTF are changed.

Next, a second embodiment of the present invention will be described.

Second Embodiment

Figure 8:
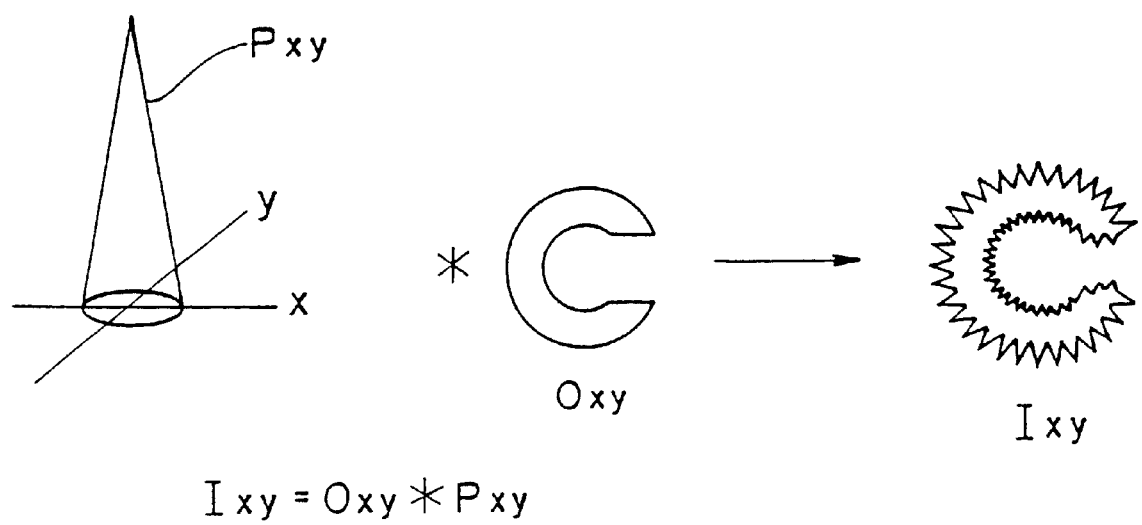
FIG. 8 shows the configuration of an optical measuring apparatus 10000 of a second embodiment of the present invention.
Figure 8:
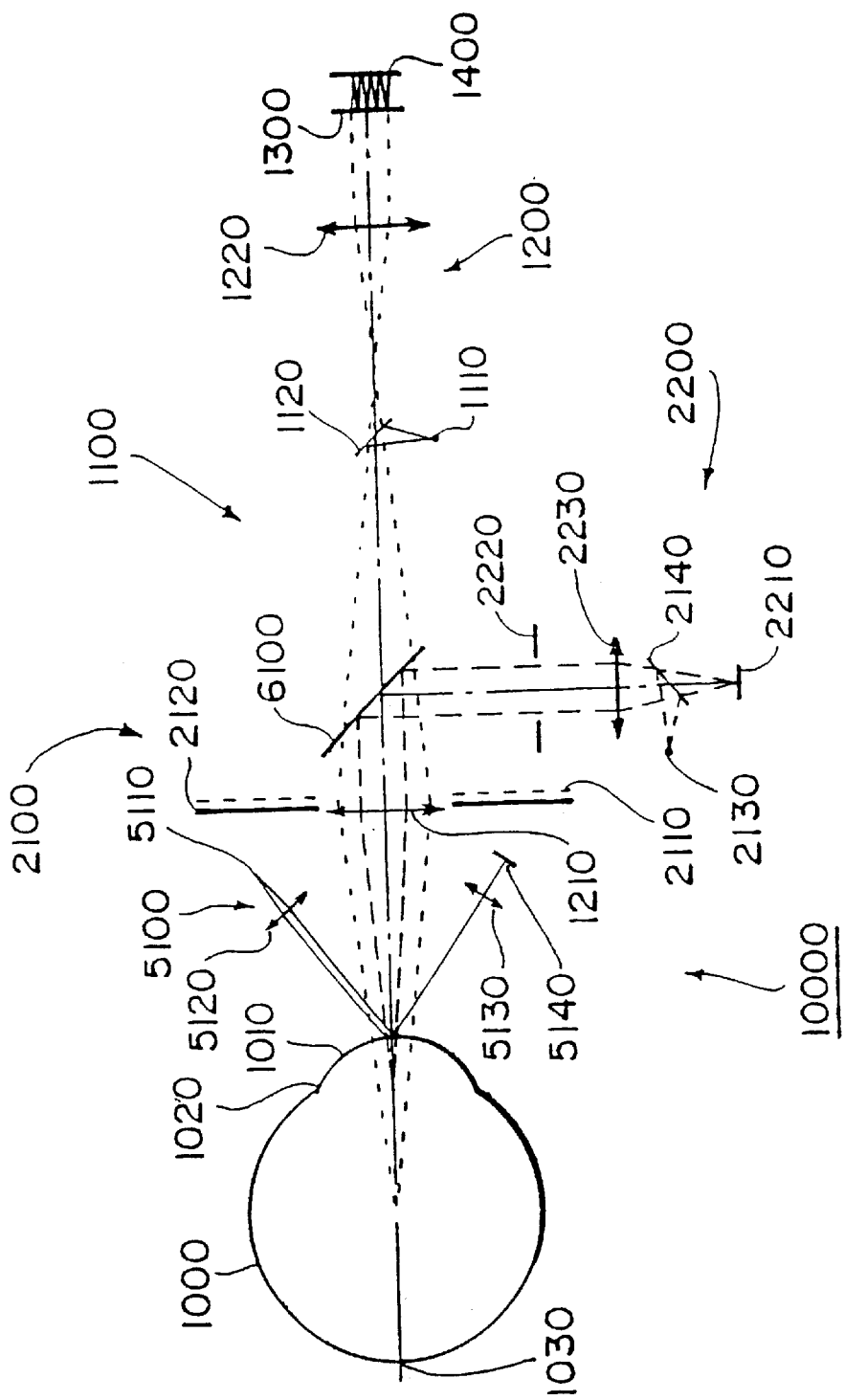
Figure 9:
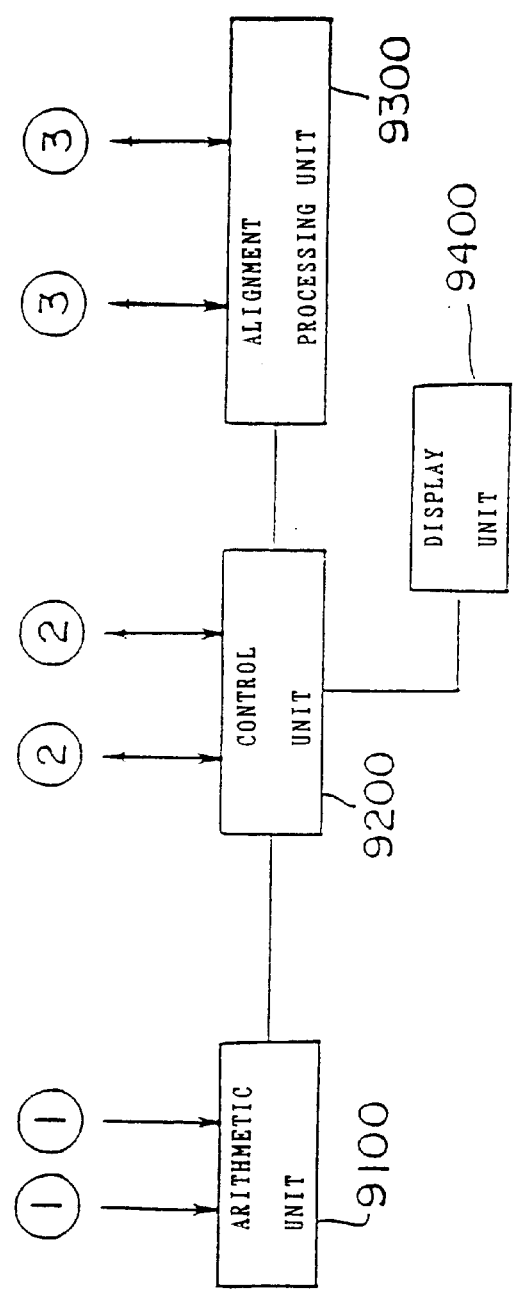
FIG. 9 is a diagram of assistance in explaining the electrical configuration of an optical measuring apparatus 10000 of a second embodiment of the present invention.

As shown in FIGS. 8 and 9, an ophthalmologic characteristic measuring apparatus 10000 according to a second embodiment of the present invention includes a first light source 1110 for emitting light rays having a first wavelength; a first illuminating optical system 1100 for convergently illuminating a portion near the center of curvature of the cornea of an eye to be examined with first illuminating light rays emitted from the first light source 1110; a first light receiving optical system 1200 for receiving the first illuminating light rays reflected from the cornea of the eye and guiding the reflected light rays to a first light receiving unit 1400; a first converting member 1300 for converting the reflected light rays into at least seventeen beams; the first light receiving unit 1400 for receiving a plurality of the light rays converted by the first converting member 1300; a second light source 2110 for emitting light rays having a second wavelength; a second illuminating optical system 2100 for projecting an index having a specific pattern on the cornea of the eye with second illuminating light rays emitted from the second light source 2110; a second light receiving optical system 2200 for receiving the second illuminating light rays reflected from the cornea of the eye and guiding the reflected light rays to a second light receiving unit 2210; the second light receiving unit 2210 for receiving the second illuminating light rays from the second light receiving optical system 2200; and an arithmetic unit 9100 for determining the shape of the cornea near the center of the eye on the basis of an inclination angle of the light rays obtained by the first light receiving unit 1400 and determining the shape of the cornea in the peripheral portion of the eye on the basis of a position of the second light receiving unit 2210 at which position the second light receiving unit 2210 receives the second illuminating light rays.

The first illuminating optical system 1100 convergently illuminates a portion near the center of curvature of the cornea of an eye to be examined with first illuminating light rays emitted from the first light source 1110. To be more specific, the first illuminating optical system 1100 allows the first illuminating light rays emitted from the first light source 1110 to be reflected from a first beam splitter 1120 and then converged to the portion near the center of the curvature of the cornea of the eye.

It may be desirable that the light source 1110 is capable of emitting light having a high spatial coherence and a low temporal coherence. The first light source 1110 of the first embodiment is a superluminescent diode (SLD), which is a point light source having a high luminance.

The first light source 1110 need not be limited to the SLD. For example, a laser which emits light having a high spatial coherence and a high temporal coherence can be employed as the first light source 1110 if a rotary diffuser or the like is inserted in an optical path to lower the temporal coherence properly and appropriately.

A light source material, such as the LED, which is low in both spatial coherence and temporal coherence, can be used if a pinhole or the like is disposed at a position of the light source on the light path, provided that the light source material such as the LED emits a large quantity of light.

The first wavelength of the light emitted from the first light source 1110 of the first embodiment may be set at, for example 780 nm.

An eye 1000 to be examined has the cornea 1010, iris 1020, and retina 1030.

The first light receiving optical system 1200 receives the first illuminating light rays reflected from the cornea 1010 of the eye and guides the reflected light rays to the first receiving unit 1400. The first light receiving optical system 1200 includes an objective lens 1210, a relay lens 1220, and a first converting member 1300 for converting the reflected light rays into at least seventeen beams.

The first light receiving optical system 1200 is preferably configured to be movable in the direction of the optical axis depending on the curvature radius of the cornea of an eye to be examined. This is effective to attain more precise measurement. The first light receiving unit 1400 or the first converting member 1300 is substantially conjugate with the cornea 1010.

As shown in FIG. 9, the arithmetic unit 9100 which is connected to a control unit 9200 calculates optical characteristics or the like on the basis of a command supplied from the control unit 9200. The control unit 9200 controls the entire apparatus including the arithmetic unit 9100. An alignment processing unit 9300 controls alignment processing.

A display unit 9400 displays data outputted from the arithmetic unit 9100. More specifically, the display unit 9400 is capable of displaying arithmetic results of optical characteristics of the eye and the shape of the cornea obtained by the arithmetic unit 9100.

The second illuminating optical system 2100 projects an index having a specific pattern on the cornea 1010 of the eye with light rays emitted from the second light source 2110.

The second light source 2110 emits light having a second wavelength different from the first wavelength of light emitted from the first light source 1110. The second light source 2110 of the first embodiment is set to emit light having a wavelength of 940 nm.

The wavelengths of the first and second light sources may be identical to each other, if light rays emitted from the first and second light sources can be separated through a diaphragm member or the like.

As the second light source 2110 of the first embodiment, an LED is employed.

The second illuminating optical system 2100 includes the second light source 2110 and a Placido's disc 2120.

Figure 10:
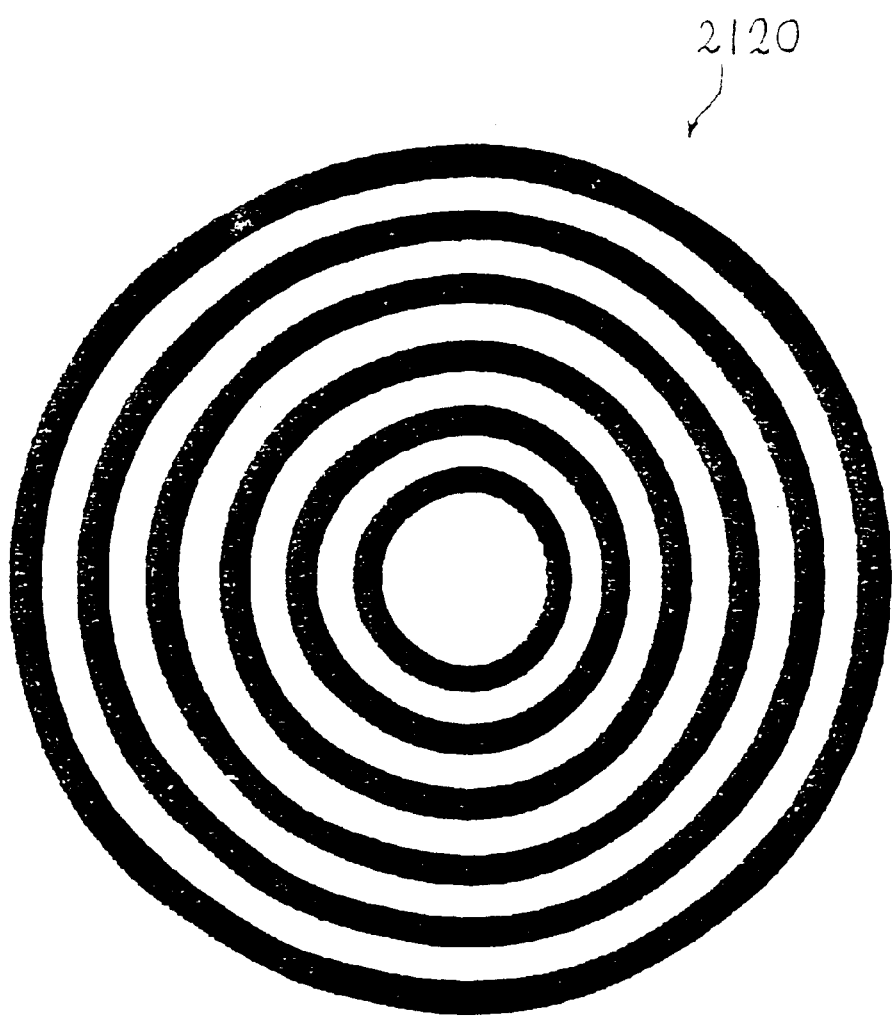
FIG. 10 is a diagram of assistance in explaining a Placido's disc.

As shown in FIG. 10, the Placido's disc 2120 is used for projecting an index having a pattern of a plurality of concentric rings. It should be noted that such an index having a pattern of a plurality of concentric rings is an illustrative example of the index having a specific pattern.

After completion of alignment (which will be described later), the above index having a pattern of a plurality of concentric rings is projected.

The second light receiving optical system 2200 receives the second illuminating light rays reflected from the cornea of the eye and guides the reflected light rays to the second light receiving unit 2210.

The second light receiving optical system 2200 includes an objective lens 1210, a first dichroic mirror 6100, a telecentric diaphragm 2220, and a relay lens 2230.

In the second light receiving optical system 2200 of the Second embodiment, the telecentric diaphragm 2220 may be arranged on the focal point on the image formation side from the objective lens 1210 (including the objective lens 1210).

The second light receiving optical system 2200 receives light rays reflected back from the cornea 1010 of the eye to be examined and guides the reflected light rays to the second light receiving unit 2210. At the time of completion of alignment, the second light receiving unit 2210 is substantially conjugate with the cornea 1010.

The second light receiving optical system 2200 also includes an XY alignment function. That is to say, the system 2200 includes the second light source 2130, a relay lens 2230, and the second light receiving unit 2210.

In addition, the second light receiving optical system 2200 of the second embodiment includes an alignment light source 2130 and a second beam splitter 2140.

The second light receiving optical system 2200 projects, after adjustment of alignment, an index of a pattern composed of a plurality of concentric rings to a portion near the cornea 1010 of an eye to be examined.

That is to say, the front eye portion observing system (second illuminating optical system 2200) has the XY alignment optical function and the Placido's observing function.

The Placido's disc having the maximum diameter of 9 mm is accurately projected on the front eye portion. Also, since the second light receiving optical system 2200 is a telecentric optical system having the telecentric diaphragm 2220, if projection of the index is slightly offset in the Z-direction, such offset does not exert any effect on measurement.

However, since a distance between the objective lens 1210 and the vertex of the cornea of the eye must be accurately adjusted, the optical system having a high accuracy is used for alignment in the Z-direction.

The second light receiving unit 2210 of the first embodiment is composed of a two-dimensional CCD, which may be, however, replaced with any one of light receiving devices.

A Z alignment optical system 5100 includes a fourth light source 5110, a collimator lens 5120, a condenser lens 513, and a linear imaging device 5140.

The converting member 1300 will be described hereinafter.

The converting member 1300 arranged in the light receiving optical system 1400 is a wavefront converting member which converts the reflected light rays into a plurality of light beams. The converting member 1300 has a plurality of micro Fresnel lenses arranged in a plane perpendicular to the optical axis.

The micro Fresnel lens will be described in detail below.

A micro Fresnel lens is an optical element having annular bands at height pitches for wavelengths and an optimized blaze at a focal point. A micro Fresnel lens which can be applied to the present invention has, for example, eight levels of optical path differences produced by semiconductor fine processing techniques, and is capable of achieving focusing at a focusing efficiency of 98% when only primary light is used.

The converting member 1300 of the first embodiment is a wavefront converting member capable of converting the reflected light rays into at least seventeen light beams.

In the first embodiment, the first converting member 1300 is a wavefront converting device capable of converting the reflected light rays into at least seventeen light beams.

The first light receiving device 1400 receives a plurality of light beams from the first converting device 1300. In the first embodiment, the light receiving device 1400 is a CCD. The CCD may be a common-CCD for TV use or a CCD having 2000×2000 elements for measurement use.

Although a CCD for TV use as the first light receiving device 1400 has a low resolution, the CCD for TV use is inexpensive and its output can be easily given to a personal computer which is used generally for image processing. NTSC image signals provided by a CCD and its driver can be easily given to a personal computer through an NTSC image input port.

Although a CCD for measurement use having 2000(2000 elements is expensive, analog signals representing measured values can be given to a personal computer if a CCD for measurement use is employed.

Signals provided by a CCD can be converted into corresponding digital signals, and the digital signals may be given to a personal computer.

The iris 1020 of the eye 1000 is substantially conjugate with the first converting device 1300 or with the first light receiving device 1400.

The first reflected light guiding optical system 1200 maintains the substantially conjugate relation between the first converting device 1300 and the iris 1020 and may be provided with an adjusting system for carrying out adjustment so that the reflected light rays from the eyeground fall in substantially parallel light rays on the light receiving device in a first light receiving state, and the reflected light rays from the cornea 1010 fall in substantially parallel light rays on the light receiving device in a second light receiving state.

The first beam splitter 6100 is inserted in the first reflected light guiding optical system 1200 to direct the light transmitted by the illuminating optical system 1100 toward the eye 1000, and to transmit the reflected light.

Next, the principle of operations of the arithmetic unit 9100 for determining the optical characteristics of the eye 1000 on the basis of the inclination of light rays provided by the first light receiving device 1400 will be described in detail.

Here, an algorithm will be described in detail.
[Hartmann's measuring principle]

Figure 11:
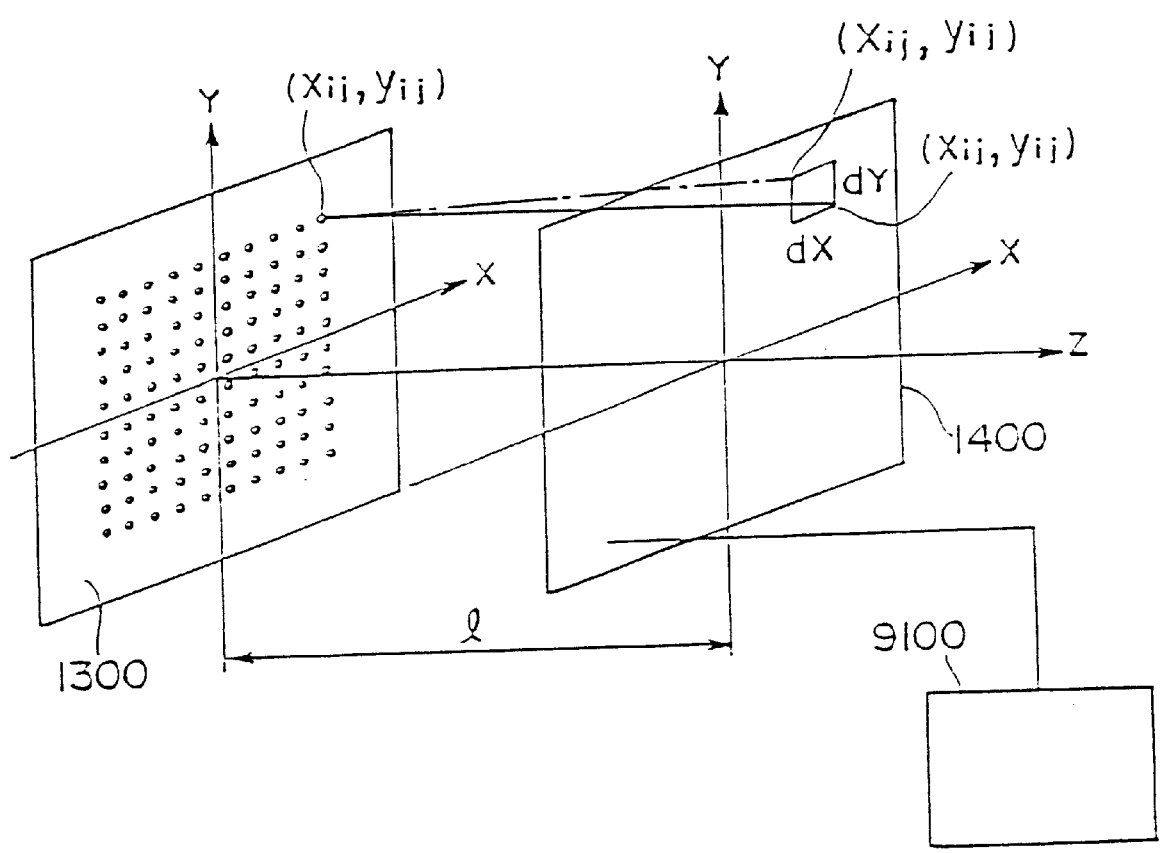
FIG. 11 is a diagram of assistance in explaining a principle.

As shown in FIG. 11, suppose that coordinates X and Y are set on the first converting device 1300, and coordinates x and y are set on the first light receiving device 1400, and a wavefront aberration is expressed by:

$$W(X, Y)$$

where X and Y are coordinates on the pupil.

Instead of W (X, Y), the following appropriate polynomial f is used.

$$W(X, Y) = f(X, Y, Z \ldots ; A, B, C \ldots)$$

where X, Y, Z ... are quantities determined by coordinates, and A, B, C ... are parameters.

Next, expression of a wave surface by the polynomial f will be examined; that is, optimum parameters (A, B, C ...) are calculated.

From the Hartmann's measuring principle, $$\frac{\partial w(X, Y)}{dX} = \frac{dx(X, Y)}{l}$$

$$\frac{\partial w(X, Y)}{dY} = \frac{dx(X, Y)}{l}$$

Equation 4

Practically, data represents inclinations and hence the derivative of each wave surface is used for calculation. In the present invention, measured data represents the inclination of light rays. The inclination can be determined by directly differentiating the wave surface at the coordinates of a position.

The wavefront sensor measures a lateral residual from a reference.

It is known that the following relation approximately holds good in FIG. 11, in which 1 is the distance between the first converting device 1300 and the first light receiving device 1400.

Values dx (X, Y) and dy (X, Y) are calculated for each element of the first converting device 1300, having a center point at X, Y, in which dx and dy are distances along the x-axis and the y-axis between a predetermined origin on the first light receiving device 1400 provided for one element of the first converting device 1300, and a point on the first light receiving device 1400 where the light beam falls on the first light receiving device 1400.

An origin corresponding to one element of the first converting device 1300 is a point on the first light receiving device 1400 where the converted light rays can be measured when the wave surface is uniformly flat, i.e., both the spherical component and the astigmatism component representing the refractive characteristic of the eye are 0 diopter, and there is no residual of irregular astigmatism, which will be described below.

Suppose that dx and dy are deviations of the light beam from the reference point. Then, $$dx(X_i, Y_j) = x_{ij} - x^0_{ij}$$

Equation 5

$$dy(X_i, Y_j) = y_{ij} - y^0_{ij}$$

Equation 6

An expression, (number of measured data)×2, can be obtained by substituting the polynomial f into the equations 5 and 6, and necessary parameters can be obtained by the method of least squares.

Although the constant term of f cannot be determined because an expression obtained by the derivative of the polynomial f is used, the determination of necessary parameters is sufficient for the present invention.

Concretely, the Zernike's polynomial, i.e., an orthogonal function properly representing aberration in terms of geometrical optics, may be used.

The general term of the Zernike's polynomial is expressed by:

$$Z_{nm}(r, \theta) = R^{n-2m}(r) \left\{ \frac{\sin}{\cos} \right\} (\pi - 2\pi)\theta$$

Equation 7 sin for $n - 2m > 0$ cos for $n - 2m \leq 0$ $$R^{n-2m}(r) = \sum_{S=0}^{m} (-1)^s \frac{(\pi - s)!}{s!(m-s)!(n-m-s)!} r^{n-2s}$$

More specifically, the Zernike's polynomial is expressed by the following expressions.

$Z_{00}=1$
$Z_{10}=x$
$Z_{11}=y$
$Z_{20}=2xy$
$Z_{21}=-1+2y^2+2x^2$
$Z_{22}=y^2-x^2$
$Z_{30}=3xy^2-x^3$
$Z_{31}=-2x+3xy^2+3x^3$
$Z_{32}=-2y+3y^3+3x^2y$
$Z_{33}=y^3-3x^2y$
$Z_{40}=4y^3X+4x^3y$
$Z_{41}=-6xy+8y^3x+8x^3y$
$Z_{42}=1-6y^2-6x^2+6y^4+12x^2y^2+6x^4$
$Z_{43}=-3y^2+3x^2+4y^4+4x^4$
$Z_{44}=y^4-6x^2y^2+x^4$

Seventeen sample points (at least sixteen sample points on four rows along the x-axis and four columns along the y-axis, and one sample point) or above are necessary when those expressions are combined by fourth degree.

Figure 12:
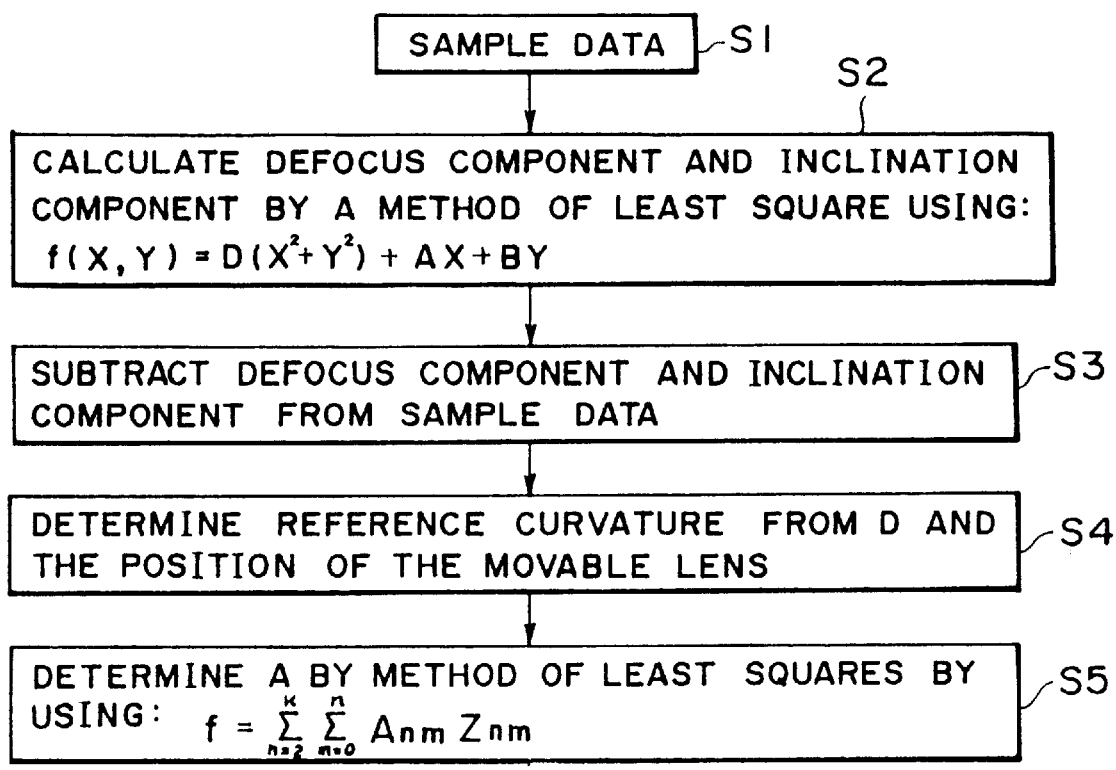
FIG. 12 is a diagram of assistance in explaining a principle.

Algorithm will be concretely described with reference to FIG. 12.

In step S1, sample data is produced on the basis of the data provided by the first light receiving device 1400. A defocus component and an inclination component are determined by the method of least squares in step S2. The defocus component and the inclination component are subtracted from the sample data in step S3. In step S4, a reference curvature is determined on the basis of D and the position of the movable lens. In step S5, A is determined by the method of least squares.

Figure 13:
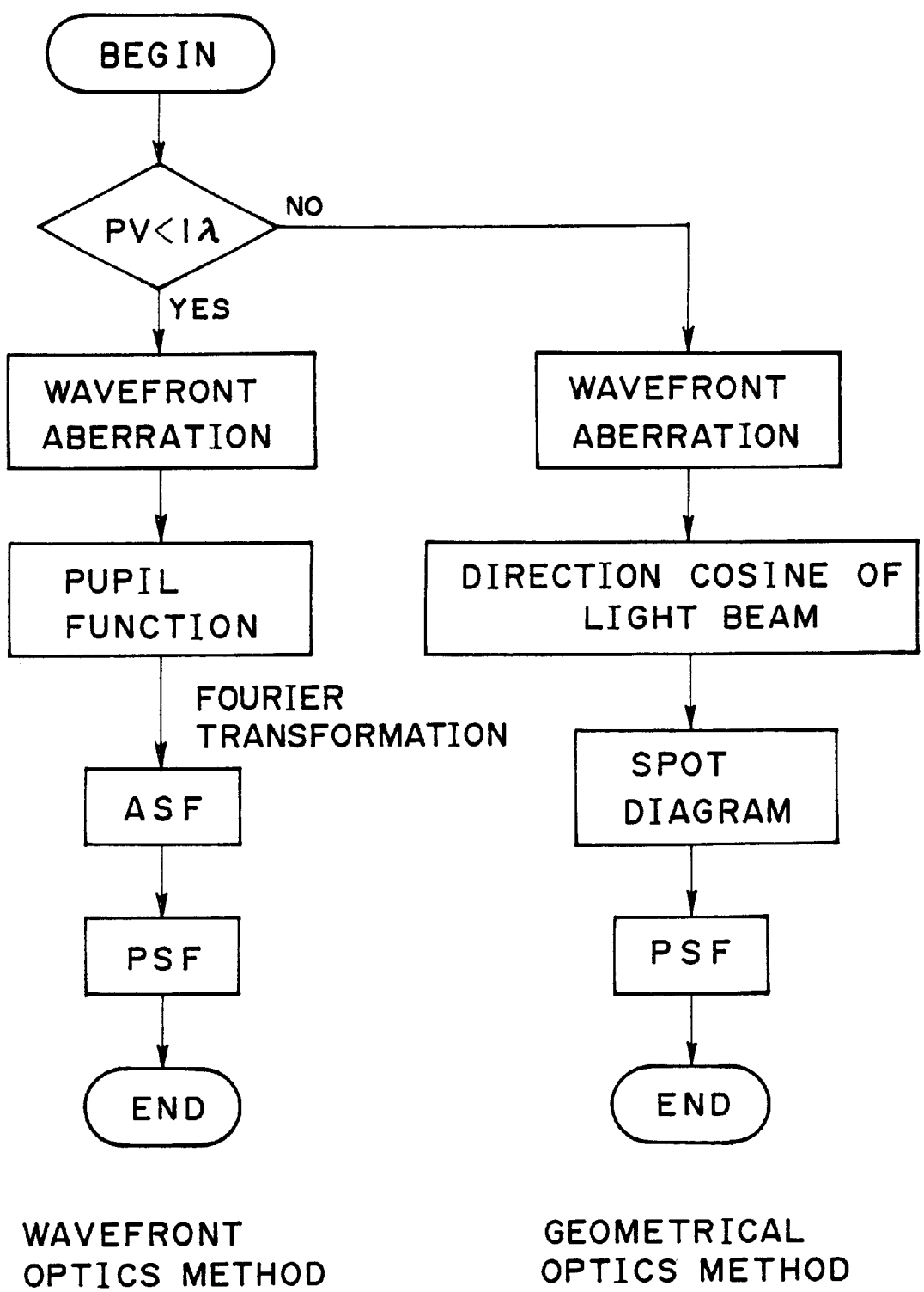
FIG. 13 is a diagram of assistance in explaining a method for determining PSF (point image intensity distribution).

Next, as in the first embodiment, a method for determining PSF (point image intensity distribution) from the wavefront aberration obtained by Hartmann's wavefront sensor (first converting device 1300) will be described with reference to FIG. 13.

In step 1 (hereinafter abbreviated as S1), arithmetic is begun. In S2,whether or not the difference (PV value) between the minimum value and the maximum value of the wavefront aberration W (X, Y) is equivalent to less than one wavelength is determined. More specifically, a wavefront optics method or a geometrical optics method is selected according to the magnitude of the wavefront aberration. Hence, when the difference (PV value) between the minimum value and the maximum value of the wavefront aberration is equivalent to less than one wavelength, the wavefront optics method is used, while when the difference (PV value) between the minimum value and the maximum value of the wavefront aberration is equivalent to one wavelength or more, the geometrical optics method is used.

When it is determined in S2 that the difference (PV value) between the minimum value and the maximum value of the wavefront aberration is equivalent to less than one wavelength, the processing proceeds to S3, where the wavefront aberration is calculated as W (X, Y) by the wavefront optics method. In S4, a pupil function is calculated by using the following expression.

$$\exp(-(i \times 2 \times \pi / \lambda \times W(X, Y)))$$

Next, in S5, the pupil function obtained in S4 is subjected to Fourier transformation, whereby ASF (point image amplitude distribution) is obtained. Then, in S6, the ASF (point image amplitude distribution) obtained in S5 is squared, whereby PSF (point image intensity distribution), an object of this process, is obtained. The processing ends in S7.

On the other hand, when it is determined in S2 that the difference (PV value) between the minimum value and the maximum value of the wavefront aberration is equivalent to one wavelength or more, the processing proceeds to S8, where the wavefront aberration is calculated as W (X, Y) by the geometrical optics method.

In S9, a direction cosine of the light beam is calculated. Specifically, since the direction cosine of the light beam corresponds to a line normal to the wave surface, the direction cosine of the light beam can be calculated as follows.

$$Pu = \frac{\partial W(X, Y)}{\partial X} - \frac{X}{17}$$

$$Pv = \frac{\partial W(X, Y)}{\partial Y} - \frac{Y}{17}$$

X and Y are coordinates on the pupi

Direction cosine =

$$\left( \frac{-Pu}{\sqrt{Pu^2 + Pv^2 + 1}}, \frac{-Pv}{\sqrt{Pu^2 + Pv^2 + 1}}, \frac{1}{\sqrt{Pu^2 + Pv^2 + 1}} \right),$$

In S10, a spot diagram in the proximity of the image surface is obtained from the direction cosine determined in S9. Then, in S11, PSF is calculated from the density of the spot diagram obtained in S10. The processing ends in S12.

Here, the description of the method for determining PSF (point image intensity distribution) from the wavefront aberration obtained by Hartmann's wavefront sensor (first converting device 1300) is concluded.

An image on the retina of the eye can be estimated from PSF (point image intensity distribution) in the same manner as that described above in the first embodiment. Therefore, its description will be omitted.

According to the present invention including the configurations described above, there are provided: an illuminating optical system for illuminating a microscopic area on the retina of the eye to be examined with light rays emitted from a light source unit; a light receiving optical system for guiding the light rays reflected from the retina of the eye to a light receiving unit; an arithmetic unit for determining optical characteristics of the eye including refractive powers and other components of the eye based on a signal from the light receiving unit, and calculating index image data representing the way in which a specified optotype is observed by the eye when a specified refractive power is corrected; and a display unit for displaying an index image representing the way in which the optotype is observed by the eye, based on the index image data. Thus, the examiner can easily understand in a single measurement the extent to which the eye to be examined can be corrected with an eyeglass lens.

In addition, according to the present invention, changes in the image of an index when the refractive power of a correction lens is changed can be displayed by arithmetic without performing another measurement. Therefore, the examiner can readily perform simulation to decide the refractive power of an eyeglass lens to be prescribed to the subject examined.

What is claimed is:

1. An ophthalmologic characteristic measuring apparatus comprising:
    a light source unit;
    an illuminating optical system for illuminating a microscopic area on the retina of the eye to be examined with light rays emitted from said light source unit;
    a light receiving optical system for guiding the light rays reflected from the retina of the eye to a light receiving unit;
    an arithmetic unit for determining optical characteristics of the eye including refractive powers and other components of the eye based on a signal from said light receiving unit, and calculating index image data representing the way in which a specified optotype is observed by the eye when a specified refractive power is corrected; and
    a display unit for displaying an index image representing the way in which the optotype is observed by the eye, based on said index image data.

2. An ophthalmologic characteristic measuring apparatus as claimed in claim 1,
    wherein said light receiving optical system forms on said light receiving unit an image resulting from the illumination of said microscopic area on the retina of the eye;
    said light receiving unit detects light quantity distribution of the image resulting from the illumination of said microscopic area on the retina of the eye; and
    said arithmetic unit determines point image intensity distribution that defines optical characteristics of the eye, based on a signal from the light receiving unit, which signal represents said light quantity distribution, and calculates from the point image intensity distribution index image data representing the way in which a specified optotype is observed by the eye when a specified refractive power is corrected.

3. An ophthalmologic characteristic measuring apparatus as claimed in claim 2, further comprising:
    focus adjusting means provided for the illuminating optical system and the light receiving optical system which change a state of focus; and a memory unit for storing a plurality of images which show light quantity distribution of images resulting from the illumination of said microscopic area on the retina of the eye and formed on the light receiving unit, in which images the amounts of adjustment by the focus adjusting means are different from one another;

wherein said arithmetic unit determines point image intensity distribution that defines optical characteristics of the eye, based on a signal representing the light quantity distribution of each of said plurality of images stored in the memory unit, and calculates from the point image intensity distribution index image data representing the way in which a specified optotype is observed by the eye when a refractive power of the eye is corrected.

4. An ophthalmologic characteristic measuring apparatus as claimed in claim 1, wherein a converting member with a plurality of openings for converting the light rays reflected from the retina of the eye into a plurality of light rays is placed in an optical path of said light receiving optical system; and said arithmetic unit determines optical characteristics of the eye based on a signal representing positions on said light receiving unit on which the plurality of reflected light rays formed by said converting member located at a distance from said light receiving unit fall, and calculates index image data representing the way in which a specified optotype is observed by the eye when a specified refractive power is corrected.

5. An ophthalmologic characteristic measuring apparatus as claimed in claim 4, wherein said arithmetic unit determines point image intensity distribution that defines optical characteristics of the eye, based on a signal representing the positions on which said plurality of reflected light rays fall, and calculates, based on the point image intensity distribution, index image data representing the way in which a specified optotype is observed by the eye when a specified refractive power is corrected.

* * * * *